(12) United States Patent
Riemer et al.

(10) Patent No.: US 6,823,037 B2
(45) Date of Patent: Nov. 23, 2004

(54) ROLLER TRUCK FOR CT SCANNER

(75) Inventors: Robert Frederick Riemer, Andover, MA (US); Simon George Harootian, Worcester, MA (US); Gilbert W. McKenna, Revere, MA (US)

(73) Assignee: Analogic Corporation, Peabody, MA (US)

( * ) Notice: Subject to any disclaimer, the term of this patent is extended or adjusted under 35 U.S.C. 154(b) by 294 days.

(21) Appl. No.: 09/882,169

(22) Filed: Jun. 15, 2001

(65) Prior Publication Data

US 2002/0146088 A1 Oct. 10, 2002

Related U.S. Application Data

(60) Provisional application No. 60/281,669, filed on Apr. 5, 2001.

(51) Int. Cl.$^7$ .................................................. A61B 6/00
(52) U.S. Cl. .............................. 378/15; 378/4; 378/20; 378/196; 378/197; 378/205
(58) Field of Search ................................ 378/4, 15, 20, 378/196, 197, 205

(56) References Cited

U.S. PATENT DOCUMENTS

| | | |
|---|---|---|
| 4,928,283 A | 5/1990 | Gordon |
| 5,109,397 A | 4/1992 | Gordon et al. |
| 5,473,657 A | 12/1995 | McKenna |
| 5,681,998 A * | 10/1997 | Nakazaki et al. .......... 73/118.1 |

* cited by examiner

Primary Examiner—Tarifur R. Chowdhury
Assistant Examiner—George Y. Wang
(74) Attorney, Agent, or Firm—McDermott Will & Emery LLP (57) ABSTRACT

A roller truck for supporting a rotating drum of a CT scanner, including a spring plate having opposing ends, top and bottom surfaces and unconstrained side edges. At least two axles are secured to the spring plate, and an attachment member is secured to the spring plate between the two axles. The attachment member is for securing the roller truck to one of a support frame of the CT scanner and the drum mounted for rotation on the frame. Rollers are rotatably mounted on each axle of the truck for supporting and allowing the instrument drum to rotate. The spring plate is free to resiliently bend about the attachment member and is adapted such that, when the instrument drum is rotated, resulting vibration frequencies are shifted by the roller truck to minimize distortions in images produced by the CT scanner.

20 Claims, 9 Drawing Sheets

ROLLER TRUCK FOR CT SCANNER

CROSS-REFERENCE TO RELATED APPLICATIONS

The present application claims priority to co-pending provisional U.S. patent application Ser. No. 60/281,669, filed Apr. 5, 2001, which is assigned to the assignee of the present disclosure and incorporated herein by reference.

FIELD OF DISCLOSURE

The present disclosure relates to the field of radiography and, in particular, relates to computer tomography ("CT") scanners. Even more particularly, the present disclosure relates to a roller truck for supporting a rotating gantry disk of a CT scanner.

BACKGROUND OF DISCLOSURE

A typical CT scanner includes a gantry comprising an annular frame for rotatably supporting an annular disk about a rotation or scanning axis of the scanner. The disk includes a central opening large enough to receive a patient extending along the scanning axis, and the disk is rotated about the patient during a scanning procedure. An x-ray tube is positioned on the disk diametrically across the central opening from an array of x-ray detectors. As the disk is rotated, the x-ray tube projects a beam of energy, or x-rays, along a scan plane, through the patient, and to the detector array. By rotating the x-ray source about the scanning axis and relative to the patient, x-rays are projected through the patient from many different directions. An image of the scanned portion of the patient can then be constructed from data provided by the detector array using a computer of the scanner.

Because even minor mechanical noise and/or artifacts causing undesirable vibration of the CT scanner during a scan can cause faulty or erroneous image information, the gantry of such a scanner typically has been provided as massively reinforced structures often weighing a ton or more in order to reduce motion due to such mechanical noise and artifacts. Consequently, because of the weight, the massive drum has usually been supported in the frame by an expensive and heavy precision roller bearing or ball bearing assembly.

Many of the disadvantages inherent in such massive, expensive, relatively fixed CT scan structures were recognized and addressed, at least in part, by the apparatus disclosed in U.S. Pat. No. 4,928,283 issued May 22, 1990 to Gordon, and in U.S. Pat. No. 5,109,397 issued Apr. 28, 1992 to Gordon, et al., both of which are assigned to the assignee of the present disclosure. In the aforesaid '283 patent, the patentee broadly suggests the use of rollers rather than bearings for rotatably supporting the drum in a frame, without however any discussion of the nature and characteristics of such rollers. The simple replacement of bearings with rollers may introduce deviations or wobble as the drum is rotated in its plane, resulting in undesirable inaccuracies in the tomographic image produced. The '397 patent addresses, inter alia, the use of electromechanical sensors that follow the outer periphery of the disc in the plane of rotation to provide compensating electrical signals for modifying or correcting the data received by the X-ray detection array.

U.S. Pat. No. 5,473,657 issued Dec. 5, 1995 to McKenna, which is assigned to the assignee of the present disclosure, discloses an improved x-ray tomography structure including a frame supporting a rotatable gantry drum. The entire mass of the drum rests upon at least two pairs of resilient rollers so that the top half of the drum is unconstrained (for centerless rotation) so as to allow the drum to freely expand and contract without introducing error-producing stresses into the drum or frame. Each pair of rollers is mounted in an elastically compliant truck, the truck being pivotably supported about a pivot axis disposed between and parallel to the rotational axes of the two rollers supported by the truck. The resilient rollers serve to (a) dampen the transfer of vibrations to the drum as the latter rotates, and (b) accommodate temperature cycling of the drum.

What is desired is a CT scanner gantry including all of the benefits of the McKenna patent, as well as additional benefits.

SUMMARY OF DISCLOSURE

The present disclosure, accordingly, provides an improved roller truck for supporting a rotating instrument drum of a CT scanner. The roller truck includes a spring plate, and an attachment member and axles secured to the spring plate. The spring plate extends between opposing ends, and includes top and bottom surfaces and unconstrained side edges extending between the opposing ends.

The axles are secured to one of the bottom and the top surfaces of the spring plate, and the attachment member is secured to one of the bottom and the top surfaces of the spring plate, between the two axles, and extends substantially parallel with each axle. The attachment member is for securing the roller truck to one of a support frame of a CT scanner and an instrument drum mounted for rotation on the support frame. Rollers are rotatably mounted on each axle for supporting and allowing the instrument drum to rotate with respect to the support frame of the CT scanner.

The spring plate is free to resiliently bend about the attachment member and is adapted such that, when the instrument drum of the CT scanner is rotated during operation of the CT scanner, the roller truck shifts vibration frequencies associated with the rotating drum away from a resonant frequency of the system. The roller truck thereby reduces distortions in reconstructed images produced by the CT scanner.

These and other features and benefits of the present disclosure will become more apparent upon reading the following specification in conjunction with the accompanying drawing figures.

BRIEF DESCRIPTION OF DRAWINGS

Like reference characters designate identical or corresponding components and units throughout the several views.

DETAILED DESCRIPTION OF DISCLOSURE

Figure 4:
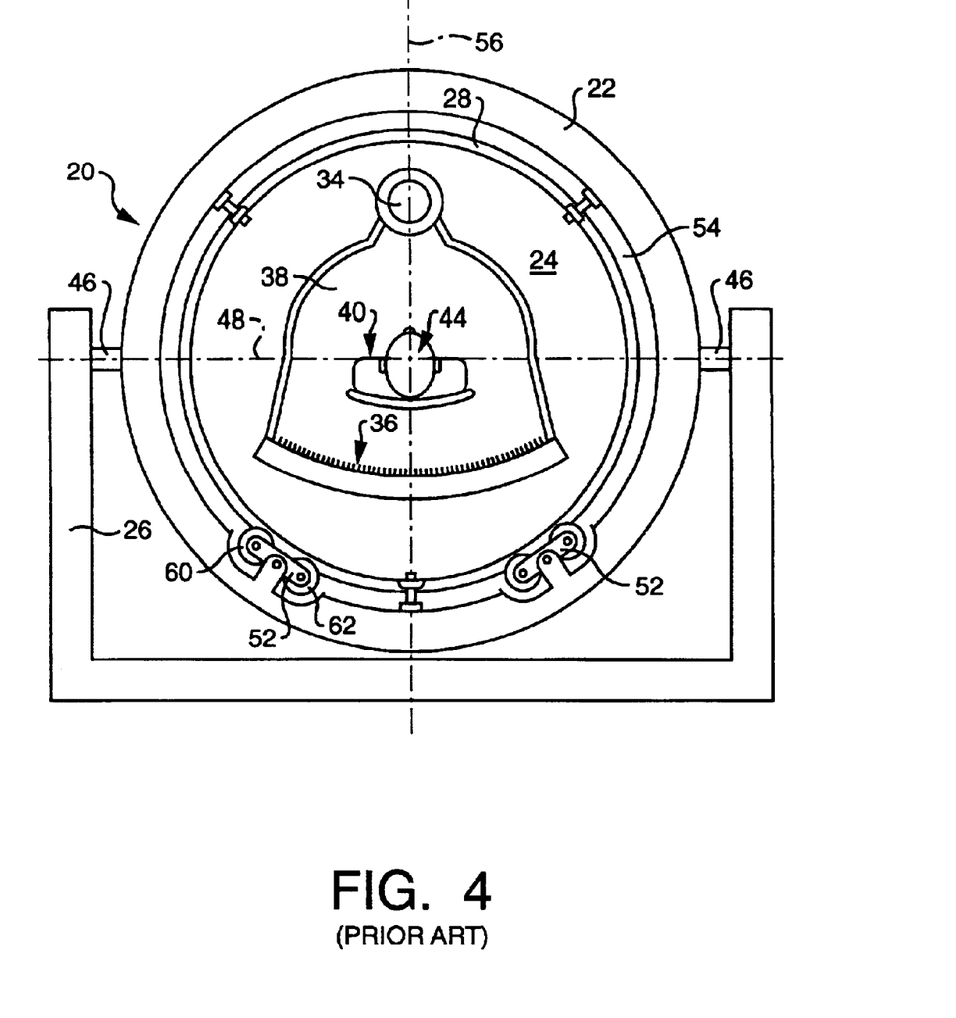
FIG. 4 is an elevation end view of a computer tomography scanner including roller trucks according to the prior art.

Referring first to FIG. 4, there is shown an annular gantry 20 of a computed tomography system (hereinafter "CT scanner") including roller trucks 52 constructed according to the prior art. The gantry 20 includes a supporting frame 22 pivotably mounted on a cart 26, and a drum 24 mounted for rotation within the support frame.

The entire mass of drum 24 is supported by gravity on the roller trucks 52, with the top half of the drum unconstrained in the rotation plane and mounted for rotation about central axis 44 relative to stationary supporting frame 22. Specifically, the frame 22 and the drum 24 are dimensioned so that the drum is rotatably mounted on the roller trucks 52 to provide an annular space 54 yielding ample clearance between the outer periphery of the drum 24 and the inner periphery of the frame 22 so that the drum is free to expand and contract as it heats and cools. Preferably, at least two roller trucks 52 are pivotably mounted on the frame 22. The trucks 52 are symmetrically positioned on opposite sides of a vertical center line 56. Each roller truck 52 comprises at least a pair of tandem rollers 60 and 62. Although not shown, at least one of the trucks 52 can be provided with a motor for turning the rollers 60 of the truck for rotating the drum 24.

Fixedly mounted on the drum 24 for rotational motion therewith are other components of the CT scanner, such as an x-ray source 34 and detector array 36. The configuration of drum 24 provides central aperture 38 preferably dimensioned so that a patient 40 on a table can be inserted therethrough. X-ray source 34 is positioned to direct a beam of x-rays through the patient 40 and to the detector array 36 as the drum is rotated during operation of the CT scanner 20.

The CT scanner 20 and the roller trucks 52 of FIG. 4 are disclosed in greater detail in U.S. Pat. No. 5,473,657 (the '657 patent), which is assigned to the assignee of the present disclosure and incorporated herein by reference in its entirety.

Figure 1:
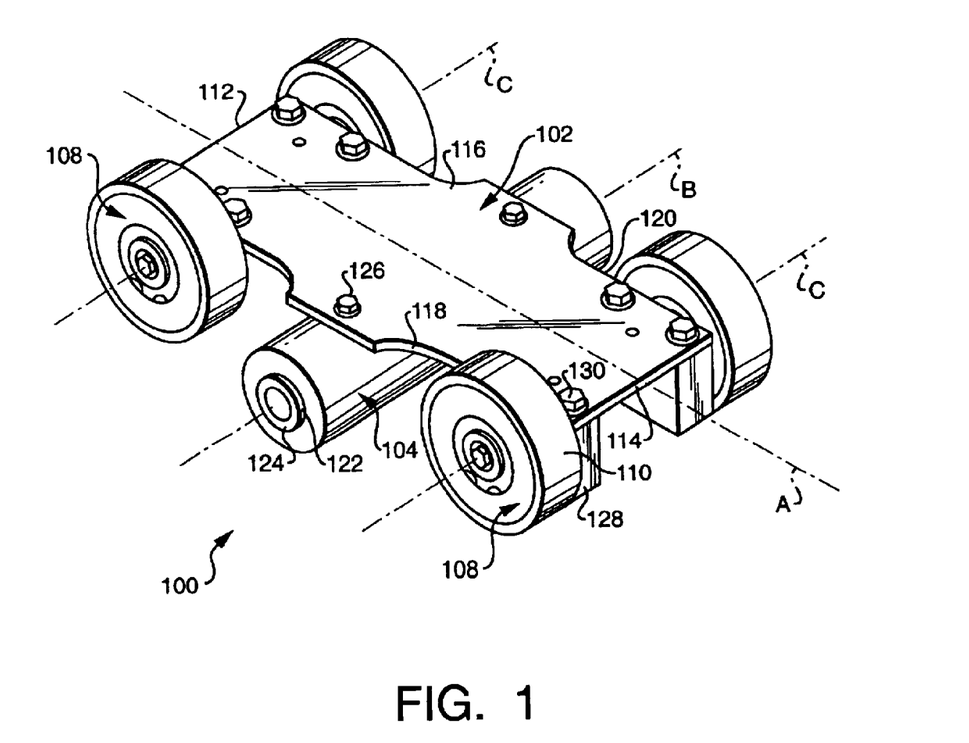
FIG. 1 is a perspective view of a roller truck constructed in accordance with the present disclosure.
Figure 2:
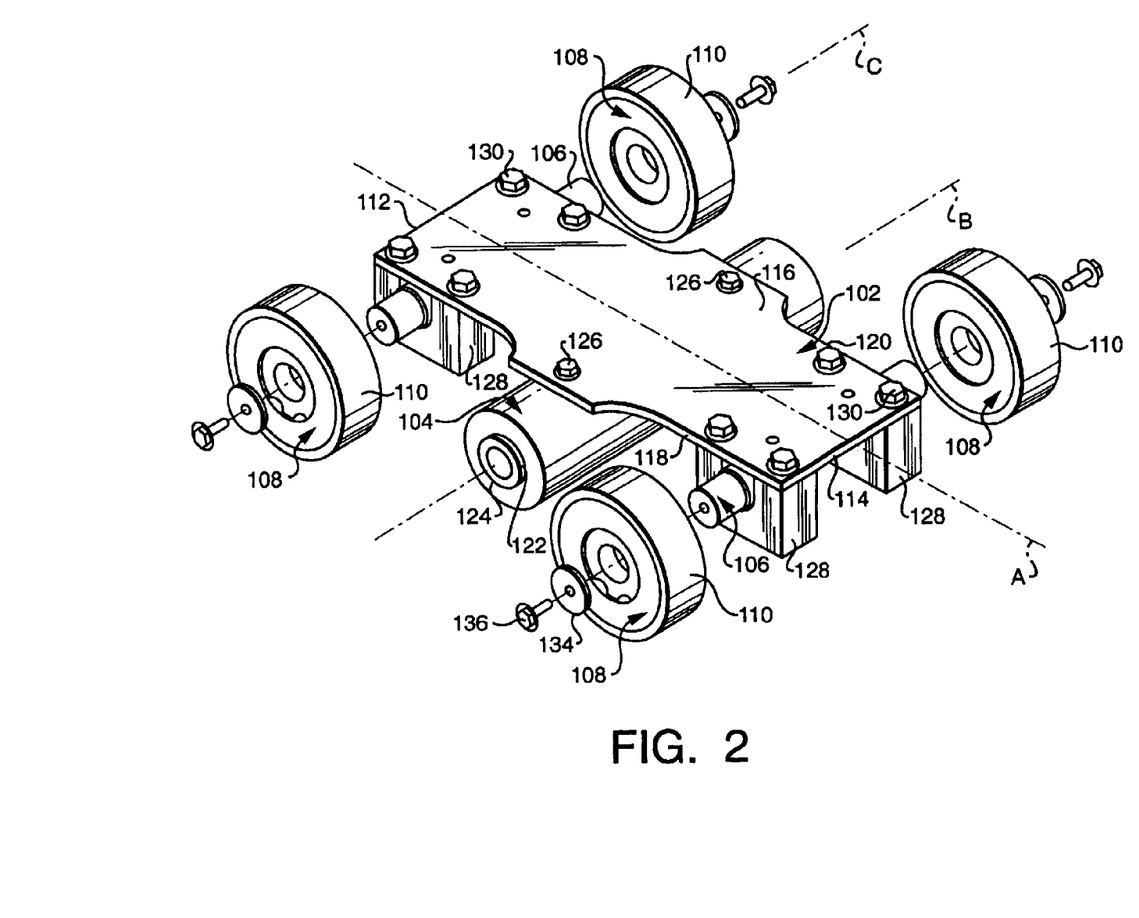
FIG. 2 is a perspective, partially exploded view the roller truck of FIG. 1.
Figure 3:
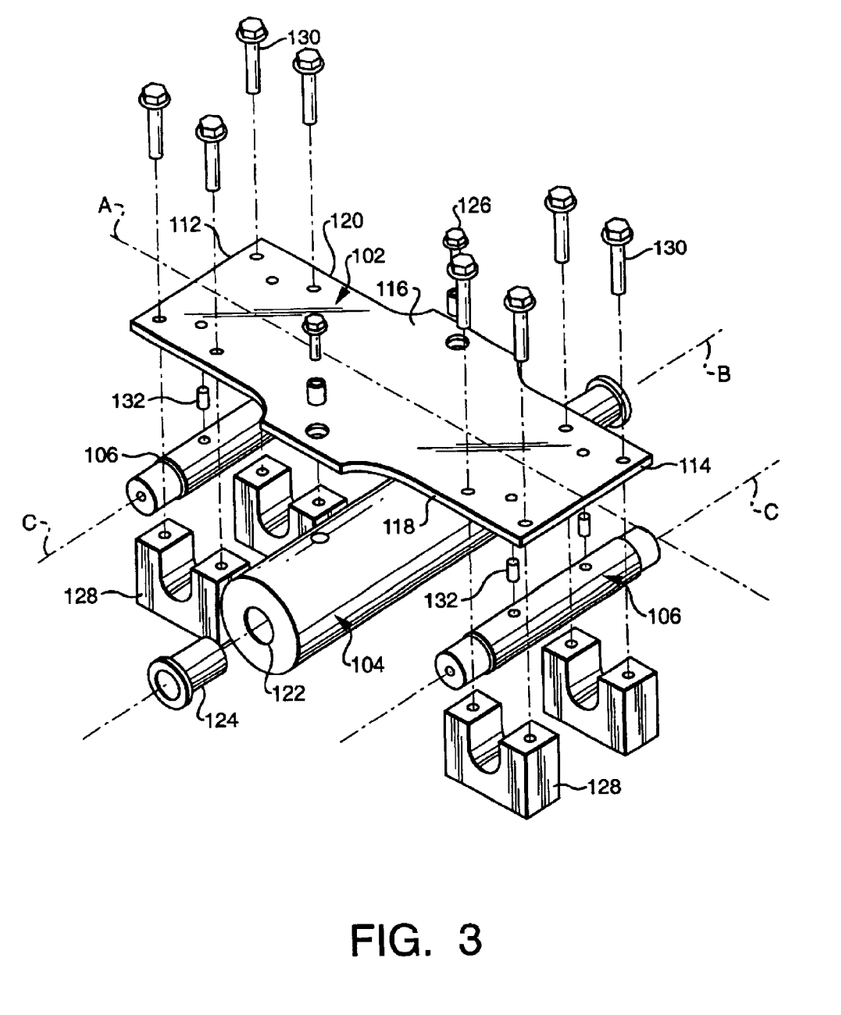
FIG. 3 is a perspective, exploded view of a portion of the roller truck of FIG. 1.

Referring to FIGS. 1 through 3, the present disclosure provides an improved roller truck 100 for supporting a rotating instrument drum of a CT scanner. The roller truck 100 includes an attachment member 104 and at least two axles 106 secured to a spring plate 102. The spring plate 102 extends between opposing ends 112, 114, and includes top and bottom surfaces 116 and unconstrained side edges 118, 120 extending between the opposing ends (the bottom surface is not viewable but is similar to the top surface 116).

The axles 106 are secured to one of the bottom and the top surfaces of the spring plate 102, and the attachment member 104 is secured to one of the bottom and the top surfaces of the spring plate, between the two axles, and extends substantially parallel with each axle. The attachment member 104 is for securing the roller truck 100 to one of a support frame of a CT scanner and an instrument drum mounted for rotation on the support frame. A pair of rollers 108 are rotatably mounted on each axle 106 for supporting and allowing the instrument drum to rotate with respect to the support frame of the CT scanner.

The spring plate 102 is free to resiliently bend about the attachment member 104 and is adapted such that, when the instrument drum of the CT scanner is rotated during operation of the CT scanner, the roller truck 100 shifts vibration frequencies associated with the rotating drum away from a resonant frequency of the CT scanner frame. The roller truck 100 thereby reduces distortions in reconstructed images produced by the CT scanner. Preferably, the roller truck 100 is adapted to shift the vibration frequencies downward.

The axles 106 are preferably secured to the bottom surface of the spring plate 102 and extend substantially parallel with the opposing ends 112, 114 of the plate (in other words, longitudinal axes "C" of the axles 106 extend perpendicular to a longitudinal axis "A" of the plates 102). The attachment member 104 is preferably also secured to the bottom surface of the spring plate 102, between the two axles 106, and extends substantially parallel with the opposing ends 112, 114 of the plate (a longitudinal axis "B" of the attachment member 104 extends parallel to the longitudinal axes "C" of the axles 106, and perpendicular to the longitudinal axis "A" of the plate 102).

Preferably, the attachment member 104 is secured approximately half way between the ends 112, 114 of the elongated spring plate 102, and the two axles 106 are secured adjacent to the ends 112, 114 of the plate and equally spaced from the attachment member 104.

The plate 102 is made of a suitably strong and durable, yet resiliently flexible material such as steel, aluminum or even plastic. Preferably, the spring plate 102 is substantially flat, but could be curved. Preferably, the spring plate 102 is elongated in that the sides 118, 120 are longer than the ends 112, 114. The plate 102 can be provide with a uniform width throughout or can, for example, include a central portion 103 that has a width greater than a width of the remainder of the plate, as shown in FIGS. 1 through 3 (alternatively, the central portion 103 could be provided with a width less than a width of the remainder of the plate). The actual dimensions of the plate 102 depend upon the plate material, the number of roller trucks 100 to be used, and the weight of the CT scanner drum and scanning instruments mounted in the drum.

The attachment member 104 is preferably tubular and includes an axial bore 122 for rotatably receiving a pin or bolt (not shown), which can then be secured to the support frame or the drum of a CT scanner. Bushing 124 can be provided in the bore 122 of the attachment member 104, as shown. The attachment member 104 may alternatively be provided as a pin for being fixed to the plate 102 and rotatably received in bearings or other suitable mounts of the gantry. In any event, in its preferred embodiment the attachment member 104 allows the roller truck 100 to pivot about the axis "B" of the attachment member.

As shown in FIGS. 1 through 3, the attachment member 104 is secured directly to the bottom surface of the spring plate 102 with bolts 126 that pass through holes in the plate 102. The axles 106 are also secured directly to the bottom surface of the spring plate 102 with U-shaped blocks 128, that are themselves attached to the plate 102 with bolts 130 that pass through holes in the plate. Dowels 132 extending through the plate 102 and into the axles 106 prevent the axles from rotating with respect to the blocks 128.

The rollers 108 are secured to the ends of the axles 106 with washers 134 and bolts 136. Each roller 108 preferably includes a tire 110 made of a resilient material, such as rubber, nylon, or suitable polymer, which acts as a shock absorber between the rotating drum and the outer annular frame of the gantry.

Figure 5:
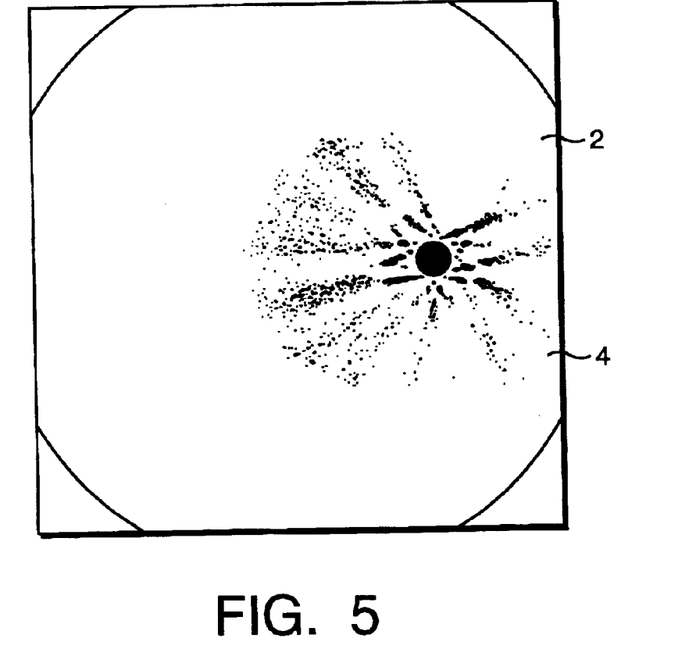
FIG. 5 shows a reconstructed image of a test scan from a CT scanner using a prior art roller truck.
Figure 6:
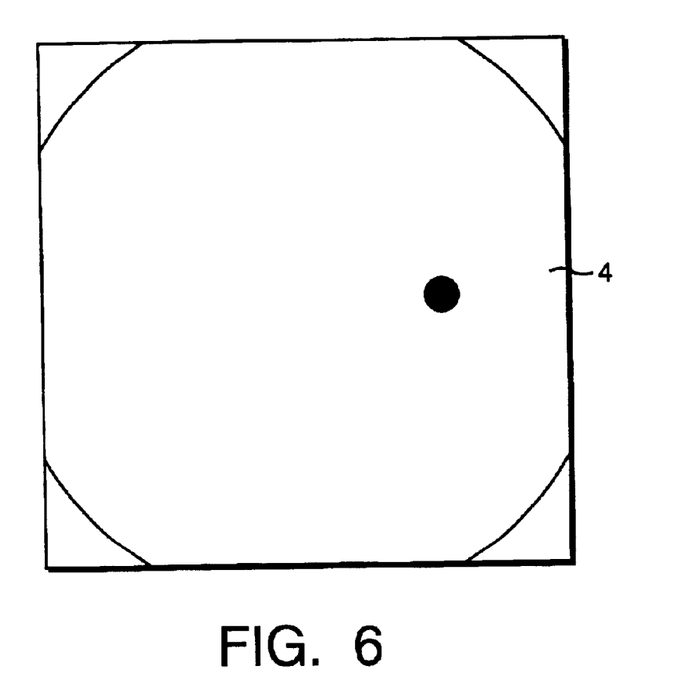
FIG. 6 shows a reconstructed image of a test scan from a CT scanner incorporating the roller truck of FIGS. 1 through 3.
Figure 7:
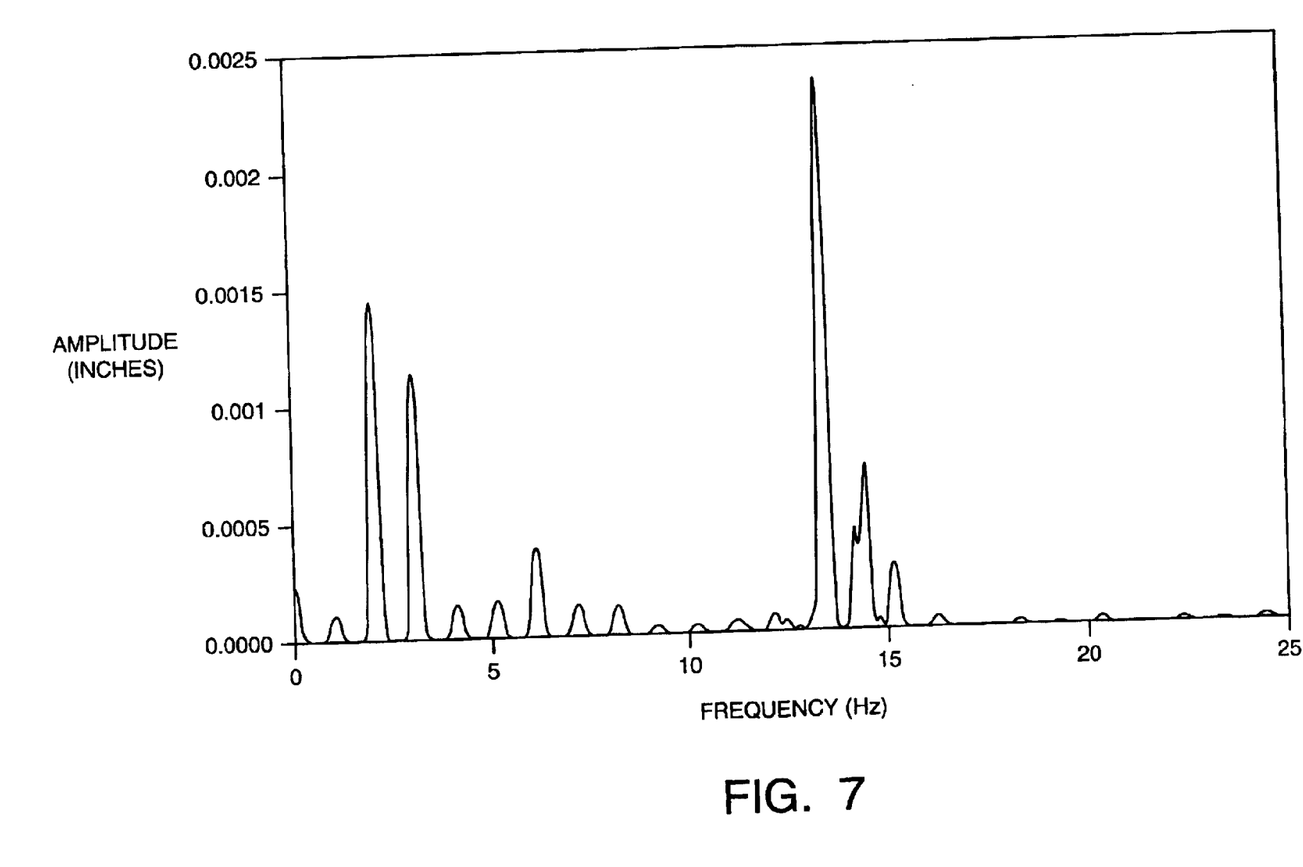
FIGS. 7 and 8 show an amplitude vs. frequency graph and an amplitude versus time graph, respectively, of a test scan from a CT scanner using a prior art roller truck.
Figure 8:
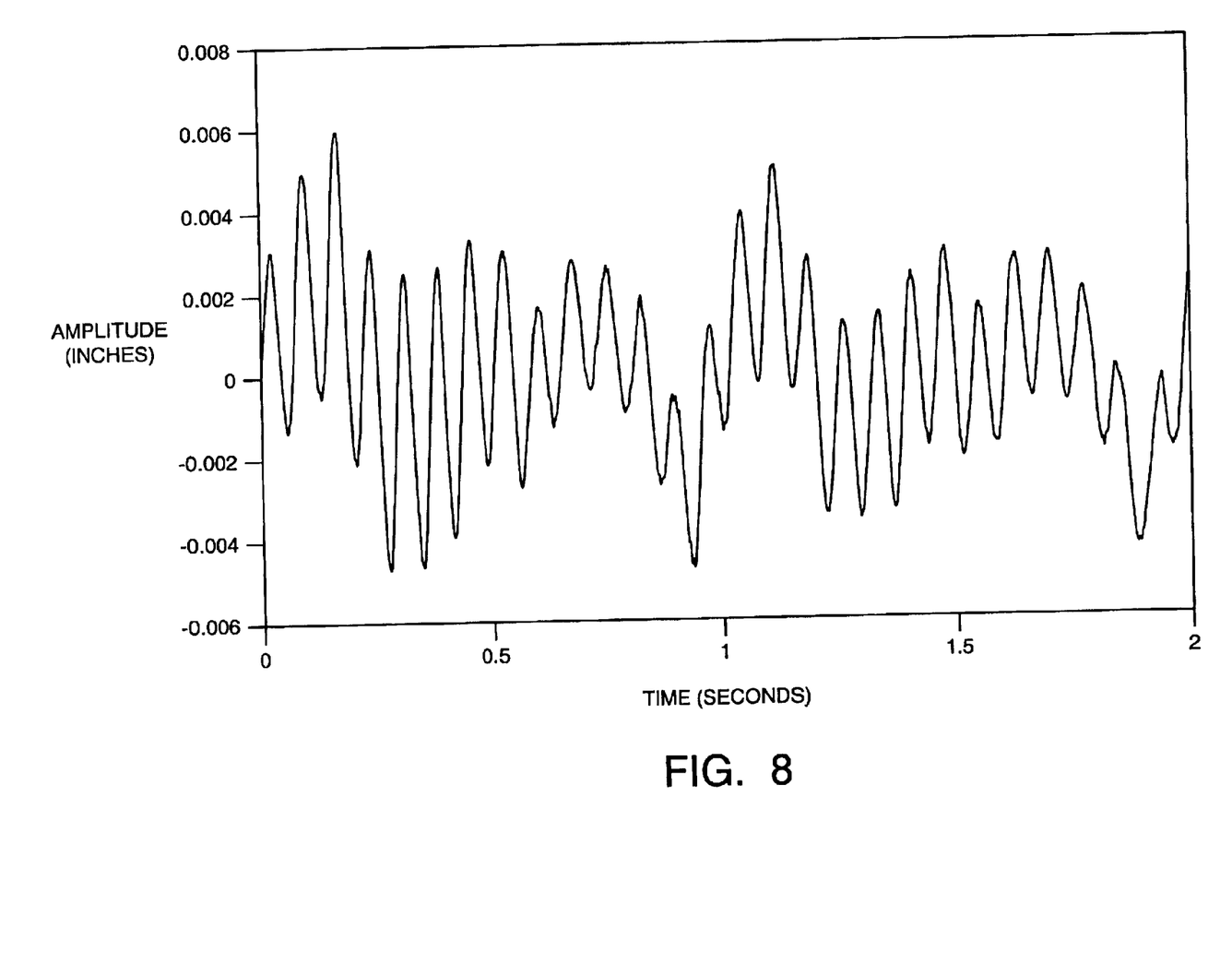
Figure 9:
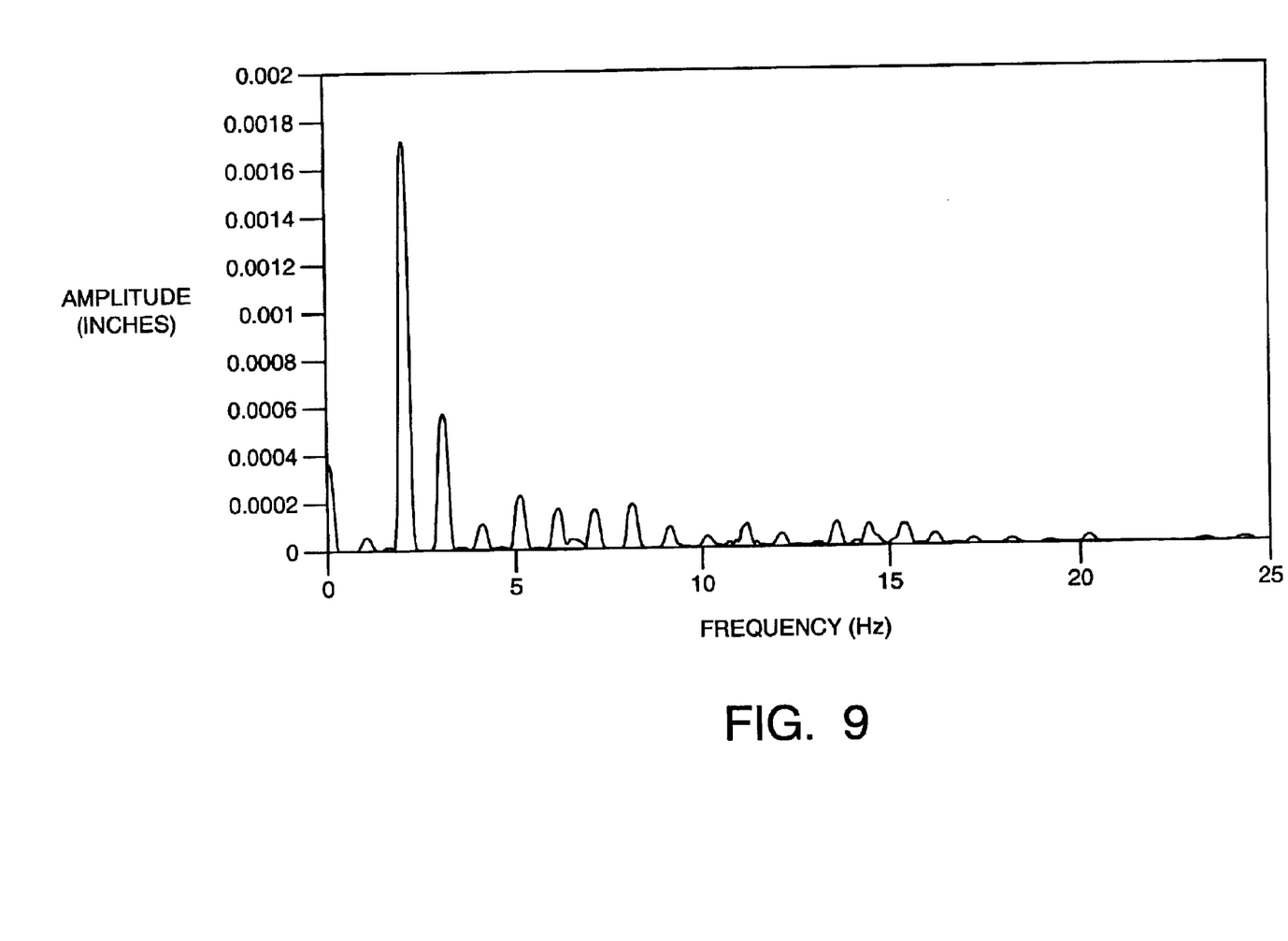
FIGS. 9 and 10 show an amplitude vs. frequency graph and an amplitude versus time graph, respectively, of a test scan from a CT scanner incorporating the roller truck of FIGS. 1 through 3.
Figure 10:
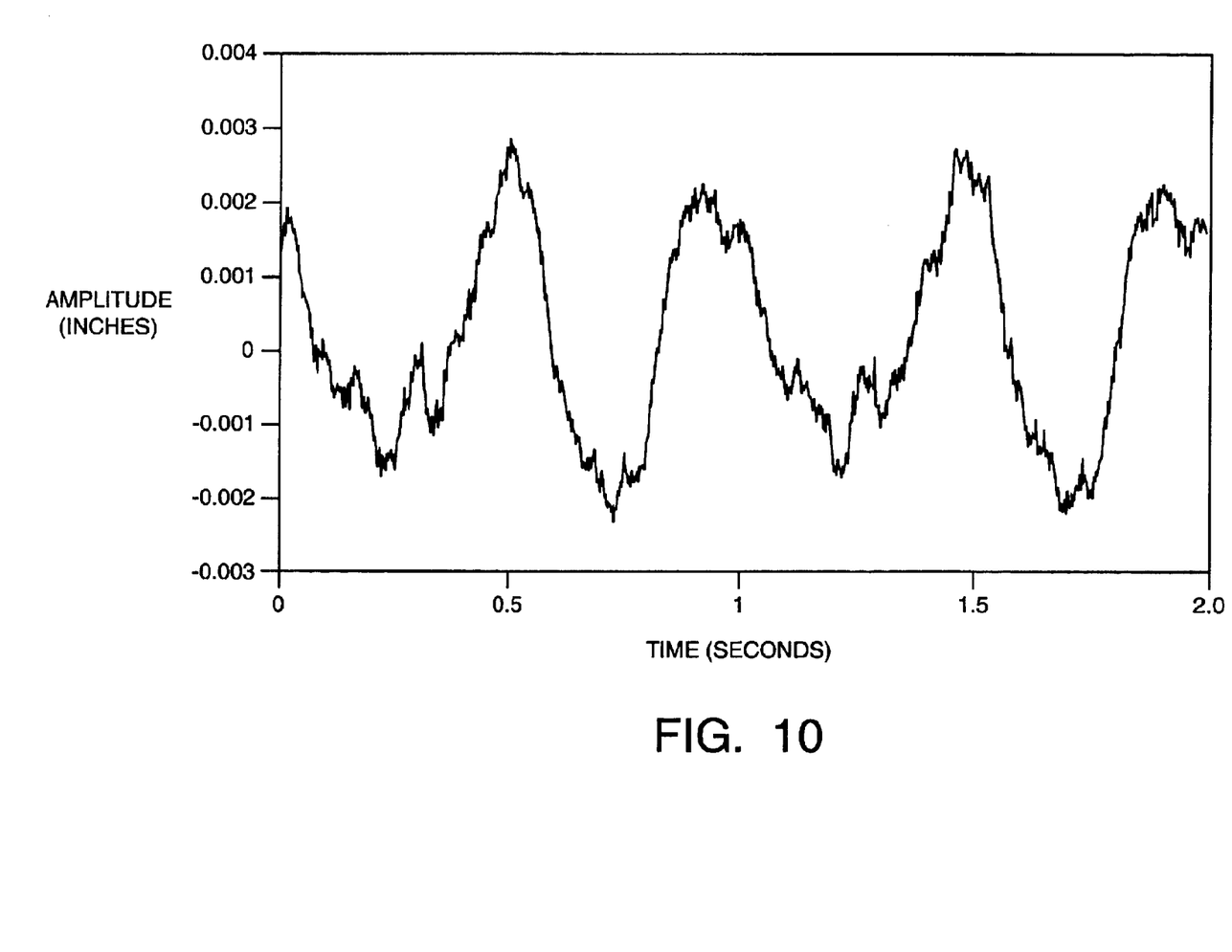

FIGS. 5 through 10 illustrate the benefits of the improved roller truck 100 of the present invention. FIGS. 7 and 8 show an amplitude vs. frequency graph and an amplitude versus time graph, respectively, of a test scan from a CT scanner using a prior art roller truck (not the roller trucks of FIG. 1), while FIGS. 9 and 10 show an amplitude vs. frequency graph and an amplitude versus time graph, respectively, of a test scan from a CT scanner incorporating the roller truck 100 of FIGS. 1 through 3. As illustrated, a CT scanner incorporating the roller truck 100 of the present disclosure has shifted the magnitude and frequencies of vibrations associated with the rotating drum downwardly.

In FIG. 5, an example of a reconstructed image of a test scan from a CT scanner using a prior art roller truck (not the roller trucks of FIG. 1) is shown. The image includes distortions, or "star artifacts" 2 surrounding a circular cross-section 4 of a rod that had been scanned. The distortions 2 in the image result at least in part from cumulative vibrations of the CT scanner reaching a resonance frequency during the scan.

In contrast, FIG. 6 shows a reconstructed image of a test scan from a CT scanner incorporating the roller truck 100 of FIGS. 1 through 3. As can be seen, the image does not include distortions surrounding the circular cross-section 4 of the scanned rod. Thus, the roller truck 100 minimize distortions in reconstructed images produced by the CT scanner.

Although not shown, the roller truck 100 of the present disclosure can be provided with a motor for turning at least one of the pairs of rollers 108 in order to rotated an instrument drum supported by the truck 100. The motor would be attached as described in the '657 patent. The present disclosure also provides improved CT scanner gantries, such as the gantry shown in the '657 patent, but including at least one roller truck 100 according to the present disclosure. Such gantries can take many forms and are not to be considered limited to the embodiment shown in the '657 patent. In general, such a gantry will include a support frame, an instrument drum, and at least one roller truck 100 for supporting the drum and allowing the drum to rotate with respect to the support frame. The support frame can have, but is not limited to, an annular shape, and the drum can be, but is not limited to, coaxially received within the support frame. In addition, the roller truck 100 can be secured to either of the support frame or the drum.

The embodiment and practices described in this specification have been presented by way of illustration rather than limitation, and various modifications, combinations and substitutions may be effected by those skilled in the art without departure either in spirit or scope from this disclosure as defined in the appended claims.

What is claimed is:

1. A gantry of a CT scanner comprising:
   a support frame:
   an annular drum mounted for rotation with respect to the support frame and having a continuous circumferential bearing surface;
   an annular disk extending radially inwardly from the drum for receiving and supporting computed tomography components; and
   a roller truck supporting the drum of of the gantry, including,
      a substantially flat single spring plate having top and bottom surfaces and unconstrained side edges extending between opposing ends, wherein a length of the plate is not greater than three times a smallest width of the plate;
      at least two axles each extending between two ends and secured to one of the bottom and the top surfaces of the spring plate, wherein said side edges of said spring plate are secured to said axles near said ends of said axles;
      an attachment member secured to the same surface of the spring plate as the axles and positioned between the two axles and extending substantially parallel with each of the axles, the attachment member securing the roller truck to the support frame of the gantry; and
      rollers rotatably mounted on each axle supporting the bearing surface of the annular drum and allowing the instrument drum to rotate with respect to the support frame of the gantry;
      wherein the spring plate is free to resiliently bend about the attachment member and is substantially flat such that, when the drum of the gantry is rotated, vibration frequencies associated with the rotating drum are shifted by the roller truck to minimize distortions in reconstructed images produced by a CT scanner incorporating the gantry.

2. A gantry according to claim 1, wherein the attachment member of the roller truck is secured to the bottom surface of the plate.

3. A gantry according to claim 1, wherein the axles of the roller truck are secured to the bottom surface of the plate.

4. A gantry according to claim 1, wherein the axles are secured to the plate adjacent the opposing ends of the plate.

5. A gantry according to claim 1, wherein the axles of the roller truck are equally spaced from the attachment member.

6. A gantry according to claim 1, wherein the attachment member of the roller truck is equally spaced from the opposing ends of the plate.

7. A gantry according to claim 1, wherein the attachment member of the roller truck is pivotally secured to the support frame such that the truck can pivot about a longitudinal axis of the attachment member.

8. A gantry according to claim 7, wherein the attachment member is tubular.

9. A gantry according to claim 1, wherein the gantry includes two of the roller trucks.

10. A gantry according to claim 1, further comprising resilient tires received on each roller.

11. A CT scanner including a gantry according to claim 1 and further comprising:
    x-ray computed tomography components operatively mounted on the annular disk of the gantry for rotation therewith.

12. A CT scanner according to claim 11, wherein the gantry includes at least two of the roller trucks.

13. A CT scanner according to claim 11, wherein the support frame is annular and the drum is coaxially received within the support frame.

14. A CT scanner according to claim 13, wherein the circumferential bearing surface of the drum faces radially outwardly and the truck is positioned between the drum and the support.

15. A CT scanner according to claim 13, wherein a space is provided between the drum and the support to allow for thermal expansion of the drum and the disk.

16. A CT scanner according to claim 11, wherein the spring plate of the truck is made from aluminum.

17. A CT scanner according to claim 11, wherein the at least one roller truck comprises two roller trucks positioned so that the trucks are equally spaced on opposite sides of a vertical center line of the drum.

18. A CT scanner according to claim 11, further comprising a motor operatively connected to the roller truck for rotating the drum.

19. A CT scanner according to claim 11, further comprising resilient tires received on each roller of the truck.

20. A CT scanner according to claim 11, and further comprising additional x-ray tomography components operatively mounted on the support frame.

* * * * *